United States Patent
Hong et al.

(10) Patent No.: US 10,054,496 B2
(45) Date of Patent: Aug. 21, 2018

(54) TEMPERATURE SENSING DEVICE, TEMPERATURE SENSOR USING THE SAME, AND WEARABLE DEVICE HAVING THE SAME

(71) Applicants: Samsung Display Co., Ltd., Yongin-si, Gyeonggi-do (KR); SNU R&DB FOUNDATION, Seoul (KR)

(72) Inventors: Jongho Hong, Yongin-si (KR); Wonsang Park, Yongin-si (KR); Jaeik Lim, Hwaseong-si (KR); Hyeyong Chu, Hwaseong-si (KR); Dae-Hyeong Kim, Icheon (KR); Jaemin Kim, Seoul (KR); Kyungsik Do, Seoul (KR); Minjoon Park, Seoul (KR)

(73) Assignees: Samsung Display Co., Ltd., Gyeonggi-do (KR); SNU R&DB Foundation, Seoul (KR)

( * ) Notice: Subject to any disclaimer, the term of this patent is extended or adjusted under 35 U.S.C. 154(b) by 270 days.

(21) Appl. No.: 14/957,919

(22) Filed: Dec. 3, 2015

(65) Prior Publication Data

US 2016/0282195 A1    Sep. 29, 2016

(30) Foreign Application Priority Data

Mar. 23, 2015 (KR) .................. 10-2015-0040276

(51) Int. Cl.
*G01K 7/00* (2006.01)
*G01K 1/00* (2006.01)
(Continued)

(52) U.S. Cl.
CPC .................. *G01K 7/16* (2013.01); *A61B 5/01* (2013.01); *G01K 13/002* (2013.01);
(Continued)

(58) Field of Classification Search
USPC .......... 374/163, 183, 100; 257/470; 977/955
See application file for complete search history.

(56) References Cited

U.S. PATENT DOCUMENTS 4,270,105 A    5/1981    Parker et al.
8,552,299 B2   10/2013   Rogers et al.
(Continued)

FOREIGN PATENT DOCUMENTS

JP    3955473 B2    5/2007
JP    4126370 B2    5/2008
(Continued)

OTHER PUBLICATIONS

Kim et al., "Electronic sensor and actuator webs for large-area complex geometry cardia mapping and therapy," *Proceedings of the National Academy of Sciences*, USA 109, 19910, 2012, pp. 1-6, and Supporting Information, pp. 1-39.
(Continued)

*Primary Examiner* — Mirellys Jagan
(74) *Attorney, Agent, or Firm* — Knobbe, Martens, Olson & Bear, LLP

(57) ABSTRACT

A temperature sensing device, temperature sensor using the same and wearable device having the same. In one aspect, the temperature sensing device includes a first layer formed of a temperature sensing material. The resistance of the temperature sensing material is configured to vary in response to changes in temperature. The temperature sensing device further includes a second layer comprising silver nano-particles and a third layer formed of the temperature sensing material. The second layer is interposed between the first and third layers.

10 Claims, 11 Drawing Sheets

(51) Int. Cl.
    *G01K 13/00*     (2006.01)
    *G01K 7/16*     (2006.01)
    *A61B 5/01*     (2006.01)
    *A61B 5/00*     (2006.01)

(52) U.S. Cl.
    CPC ...... *A61B 5/0008* (2013.01); *A61B 2560/0412* (2013.01); *A61B 2562/0285* (2013.01); *A61B 2562/164* (2013.01)

(56) References Cited

U.S. PATENT DOCUMENTS

| | | | |
|---|---|---|---|
| 8,761,963 B2 | 6/2014 | Hinkel, III | |
| 2011/0315985 A1 | 12/2011 | Oba et al. | |
| 2013/0281815 A1* | 10/2013 | Varadan | A61B 5/04085 600/388 |
| 2016/0052131 A1* | 2/2016 | Lessing | B25J 9/142 361/679.01 |
| 2017/0354372 A1* | 12/2017 | Varadan | A61B 5/0408 |

FOREIGN PATENT DOCUMENTS

| | | |
|---|---|---|
| KR | 10-2015-0002972 A | 1/2015 |
| WO | WO 2011/025132 A1 | 3/2011 |
| WO | WO 2011/118884 A1 | 9/2011 |
| WO | WO 2012/087065 A2 | 6/2012 |
| WO | WO 2013/129795 A1 | 9/2013 |

OTHER PUBLICATIONS

Lim et al., "Transparent and Stretchable Interactive Human Machine Interface Based on Patterned Graphene Heterostructures," Supporting Information, Adv. Funct. Mater., DOI: 10.1002/adfm. 201402987, 2014, 21 pages.

Park et al., "Oxide Nanomembrane Hybrids with Enhanced Mechano- and Thermo-Sensitivity for Semitransparent Epidermal Electronics," Submitted to *Advanced Materials*.

Yeo et al., "Multifunctional Epidermal Electronics Printed Directly Onto the Skin," *Adv. Mater.* 2013, 25, 2773-2778.

Kim et al., "Stretchable silicon nanoribbon electronics for skin prosthesis," *Nature Communications*, DOI: 10.1038/ncomms6747, published Dec. 9, 2014, pp. 1-11.

Lipomi et al., "Skin-like pressure and strain sensors based on transparent elastic films of carbon nanotubes," *Nature Nanotechnology*, DOI: 10 1038/NNANO.2011.184, published online Oct. 23, 2011, pp. 788-792.

Tien et al., "A Flexible Bimodal Sensor Array for Simultaneous Sensing of Pressure and Temperature," *Adv. Mater.* 2014, 26, pp. 796-804.

Webb et al., "Ultrathin conformal devices for precise and continuous thermal characterization of human skin," *Nature Materials*, DOI: 10.1038/NMATG3755, published online Sep. 2013, pp. 938-944 & Erratum.

\* cited by examiner

TEMPERATURE SENSING DEVICE, TEMPERATURE SENSOR USING THE SAME, AND WEARABLE DEVICE HAVING THE SAME

CROSS-REFERENCE TO RELATED APPLICATION

This U.S. non-provisional patent application claims priority under 35 U.S.C. § 119 of Korean Patent Application No. 10-2015-0040276, filed on Mar. 23, 2015, the contents of which are hereby incorporated by reference in its entirety.

BACKGROUND

Field

The present disclosure generally relates to a temperature sensing device and a temperature sensor using the same.

Description of the Related Technology

In general, temperature sensors are manufactured using platinum, gold, single-crystalline silicon, etc. As such, the manufacturing of temperature sensors is relatively costly and these sensors are not transparent.

When the standard temperature sensor is manufactured to be transparent, it involves casting an organic material into a mold and drying the organic material. Accordingly, it is difficult to reduce the size of and mass-produce the standard temperature sensor. To overcome those disadvantages, a temperature sensing device formed using an oxide material has been developed. Oxide materials have good characteristics at temperatures equal to or greater than about 300° Celsius, making it difficult to use the materials in a flexible device.

SUMMARY OF CERTAIN INVENTIVE ASPECTS

One inventive aspect is a temperature sensing device having improved temperature sensing ability.

Another aspect is a temperature sensing device including silver nano-particles to improve a temperature sensing ability.

Another aspect is a temperature sensing device having flexibility and being transparent or semi-transparent.

Another aspect is a temperature sensor having the temperature sensing device.

Another aspect is a wearable device having the temperature sensor.

Another aspect is a temperature sensing device including a first layer including a temperature sensing material in which a resistance is varied depending on a temperature, a second layer including silver nano-particles, and a third layer including the temperature sensing material. The second layer can be interposed between the first and third layers.

The temperature sensing material can include zinc oxide ($ZnO_x$) doped with an aluminum oxide ($Al_2O_3$).

The temperature sensing material can include zinc oxide ($ZnO_x$) doped with aluminum oxide of about 1 wt %.

The second layer can include silver nano-particles diluted with a constant dilution ratio.

The silver nano-particles of the second layer can be diluted with a dilution ratio of about 1000:1 to about 10:1.

Each of the first, second, and third layers can be transparent or semi-transparent.

Another aspect is a temperature sensor including a first film having a flexibility, a first electrode formed on the first film, a second electrode formed on the first film and spaced apart from the first electrode, at least one temperature sensing devices formed on the first film, the first electrode, and the second electrode, and a second film formed on the temperature sensing device. The temperature sensing device can include a first layer including a temperature sensing material in which a resistance is varied depending on a temperature, a second layer including silver nano-particles, and a third layer including the temperature sensing material. The second layer can be interposed between the first and third layers.

The temperature sensing material can include zinc oxide ($ZnO_x$) doped with an aluminum oxide ($Al_2O_3$).

The temperature sensing material can include zinc oxide ($ZnO_x$) doped with aluminum oxide of about 1 wt %.

The second layer can include silver nano-particles diluted with a constant dilution ratio.

The silver nano-particles of the second layer can be diluted with a dilution ratio of about 1000:1 to about 10:1.

The first and second electrodes can have a serpentine structure.

The first and second films can have a serpentine structure.

The temperature sensing device can be transparent or semi-transparent.

Another aspect is a wearable device includes a temperature sensor sensing a temperature and a controller detecting the temperature using the temperature sensor and carrying out a command corresponding to the temperature. The temperature sensor can include a first film having a flexibility, a first electrode formed on the first film, a second electrode formed on the first film and spaced apart from the first electrode, a first layer formed on the first film, the first electrode, and the second electrode and including a temperature sensing material in which a resistance is varied depending on a temperature, a second layer formed on the first layer and including silver nano-particles, a third layer formed on the second layer and including the temperature sensing material, and a second film formed on the third layer.

The temperature sensing material can include zinc oxide ($ZnO_x$) doped with an aluminum oxide ($Al_2O_3$).

The temperature sensing material can include zinc oxide ($ZnO_x$) doped with aluminum oxide of about 1 wt %.

The second layer can include the silver nano-particles diluted with a constant dilution ratio.

The silver nano-particles of the second layer can be diluted with a dilution ratio of about 1000:1 to about 10:1.

The first and second electrodes can have a serpentine structure.

The first and second films can have a serpentine structure.

The temperature sensing device can be transparent or semi-transparent.

The wearable device can further include a storing part storing data. The controller can control the storing part to allow the storing part to store the detected temperature by time when the detected temperature using the temperature sensor is in a normal range.

The wearable device can further include a communicating part communicating with an external device. The controller can communicate with the external device through the communicating part when the detected temperature using the temperature sensor is not in the normal range.

Another aspect is a temperature sensing device, comprising a first layer formed of a temperature sensing material, wherein the resistance of the temperature sensing material is configured to vary in response to changes in temperature; a second layer comprising silver nano-particles; and a third layer formed of the temperature sensing material, wherein the second layer is interposed between the first and third layers.

In exemplary embodiments, the temperature sensing material comprises zinc oxide ($ZnO_x$) doped with aluminum oxide ($Al_2O_3$). The zinc oxide ($ZnO_x$) of the temperature sensing material can be doped with the aluminum oxide at about 1 wt %. The silver nano-particles of the second layer can be diluted with a substantially constant dilution ratio. The silver nano-particles of the second layer can be diluted with a dilution ratio of about 1000:1 to about 10:1. Each of the first, second, and third layers can be transparent or semi-transparent.

Another aspect is a temperature sensor, comprising a first film that is flexible; a first electrode formed over; a second electrode formed over the first film and spaced apart from the first electrode; at least one temperature sensing component formed over the first film, the first electrode, and the second electrode; and a second film formed over the temperature sensing component, wherein the temperature sensing component comprises: a first layer formed of a temperature sensing material, wherein the resistance of the temperature sensing material is configured to vary in response to changes in temperature; a second layer comprising silver nano-particles; and a third layer formed of the temperature sensing material, wherein the second layer is interposed between the first and third layers.

In exemplary embodiments, the temperature sensing material comprises zinc oxide ($ZnO_x$) doped with aluminum oxide ($Al_2O_3$). The zinc oxide ($ZnO_x$) of the temperature sensing material can be doped with the aluminum oxide at about 1 wt %. The silver nano-particles of the second layer can be diluted with a substantially constant dilution ratio. The silver nano-particles of the second layer can be diluted with a dilution ratio of about 1000:1 to about 10:1. The first and second electrodes can have a serpentine structure. The first and second films can have a serpentine structure. The temperature sensing device can be transparent or semi-transparent.

Another aspect is a wearable device, comprising a temperature sensor configured to sense temperature; and a controller configured to: i) detect the temperature using the temperature sensor and ii) carry out a command corresponding to the sensed temperature, wherein the temperature sensor comprises: a first film that is flexible; a first electrode formed over the first film; a second electrode formed over the first film and spaced apart from the first electrode; a first layer formed over the first film, the first electrode, and the second electrode, wherein the first layer is formed of a temperature sensing material and wherein the resistance of the temperature sensing material is configured to vary in response to changes in temperature; a second layer formed over the first layer and comprising silver nano-particles; and a third layer formed over the second layer and formed of the temperature sensing material; and a second film formed over the third layer.

In exemplary embodiments, the temperature sensing material comprises zinc oxide ($ZnO_x$) doped with aluminum oxide ($Al_2O_3$). The zinc oxide ($ZnO_x$) of the temperature sensing material can be doped with the aluminum oxide at about 1 wt %. The silver nano-particles of the second layer can be diluted with a substantially constant dilution ratio. The silver nano-particles of the second layer can be diluted with a dilution ratio of about 1000:1 to about 10:1. The first and second electrodes have a serpentine structure. The first and second films can have a serpentine structure. The temperature sensing device can be transparent or semi-transparent.

In exemplary embodiments, the wearable device further comprises a memory configured to store temperature data, wherein the controller is further configured to control the memory to store the detected temperature as a function of time when the detected temperature using the temperature sensor is in a normal range.

In exemplary embodiments, the wearable device further comprises a communication interface configured to communicate with an external device, wherein the controller is further configured to communicate with the external device through the communication interface when the detected temperature using the temperature sensor is not in the normal range.

According to at least one embodiment, the temperature sensing device and the temperature sensor can have superior temperature sensing ability.

In addition, the temperature sensing device and the temperature sensor can be mass-produced with a lower cost.

Further, the temperature sensing device and the temperature sensor can have the flexibility and may be transparent or semi-transparent.

BRIEF DESCRIPTION OF THE DRAWINGS

The above and other advantages of the present disclosure will become readily apparent by reference to the following detailed description when considered in conjunction with the accompanying drawings.

DETAILED DESCRIPTION OF CERTAIN INVENTIVE EMBODIMENTS

The following description with reference to the accompanying drawings is provided to facilitate a comprehensive understanding of various embodiments of the present disclosure as defined by the claims and their equivalents. It includes various specific details to facilitate that understanding but these are to be regarded as merely exemplary. Accordingly, those of ordinary skill in the art will recognize that various changes and modifications of the various embodiments described herein can be made without departing from the scope and spirit of the present disclosure. In addition, descriptions of well-known functions and constructions may be omitted for clarity and conciseness.

The terms and words used in the following description and claims are merely used to enable a clear and consistent understanding of the present disclosure. Accordingly, it should be apparent to those skilled in the art that the following description of various embodiments of the present disclosure is provided for illustration purpose only and not for the purpose of limiting the present disclosure as defined by the appended claims and their equivalents.

Hereinafter, the described technology will be explained in detail with reference to the accompanying drawings.

Figure 1:
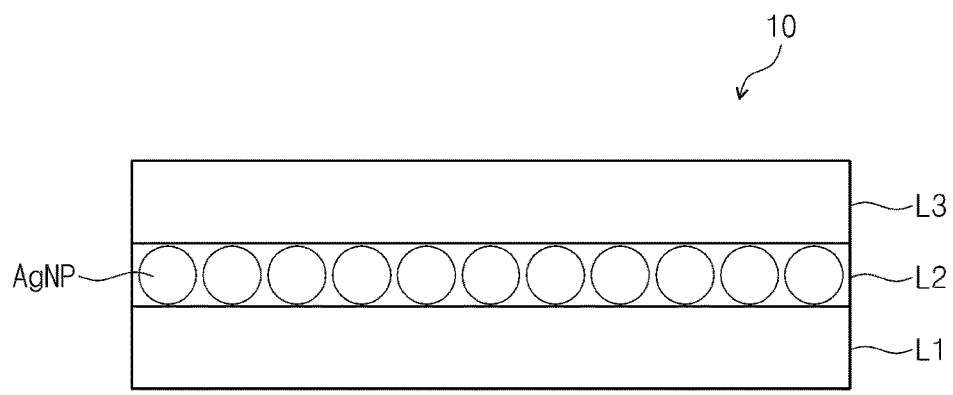
FIG. 1 is a cross-sectional view showing a temperature sensing device according to an exemplary embodiment of the present disclosure.

FIG. 1 is a cross-sectional view showing a temperature sensing device 10 according to an exemplary embodiment of the present disclosure.

Referring to FIG. 1, the temperature sensing device or temperature sensing component 10 includes first, second, and third layers L1, L2, and L3, each including a temperature sensing material. The temperature sensing device 10 has a structure in which the first to third layers L1 to L3 are sequentially stacked.

The first to third layers L1 to L3 include the temperature sensing material in which a resistance thereof varies depending on temperature. The first and third layers L1 and L3 include zinc oxide ($ZnO_x$) doped with aluminum oxide ($Al_2O_3$) as the temperature sensing material. In the embodiment of FIG. 1, zinc oxide ($ZnO_x$) is doped with aluminum oxide at about 1 wt %. Hereinafter, for the convenience of explanation, zinc oxide ($ZnO_x$) being doped with aluminum oxide at about 1 wt % is referred to as aluminum doped zinc oxide (AZO).

The second layer L2 is interposed between the first and third layers L1 and L3 and includes silver nano-particles (AgNP). The silver nano-particles (AgNP) are diluted with a substantially constant dilution ratio and are included in the second layer L2. Here, the dilution ratio indicates the dilution degree of the silver nano-particles (AgNP) in the second layer L2. In the present exemplary embodiment, the dilution ratio of the silver nano-particles (AgNP) included in the second layer L2 can be in the range of about 1000:1 to about 10:1.

The first to third layers L1 to L3 can be transparent or semi-transparent. In addition, the first and third layers L1 and L3 can have a thickness of about 300 nm or less and each silver nano-particle (AgNP) included in the second layer L2 can have a diameter of about 10 nm or less. The first to third layers L1 to L3 can be formed by a thin film deposition process using a standard micro-processing technology. Accordingly, the temperature sensing device 10 can be mass produced with a low manufacturing cost.

The temperature sensing device 10 including the second layer L2 in which the silver nano-particles (AgNP) are diluted with the substantially constant dilution ratio are included has superior temperature sensing ability. This will be described in detail later with reference to FIGS. 5B and 5C.

Figure 2:
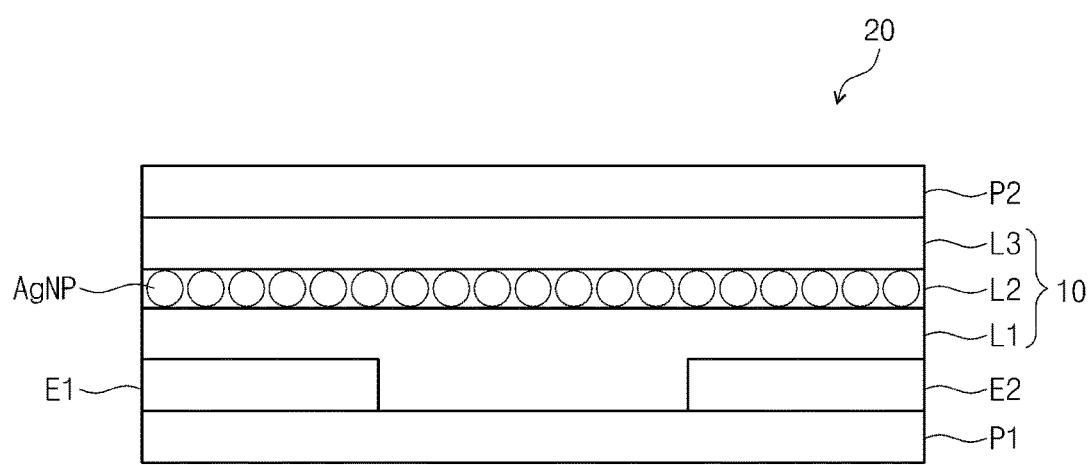
FIG. 2 is a cross-sectional view showing a temperature sensor including the temperature sensing device shown in FIG. 1.

FIG. 2 is a cross-sectional view showing a temperature sensor 20 including the temperature sensing device 10 shown in FIG. 1.

Referring to FIG. 2, the temperature sensor 20 includes first and second films P1 and P2, first and second electrodes E1 and E2, and the temperature sensing device 10.

The first and second films P1 and P2 include a transparent or semi-transparent material, such as polydimethylsiloxane (PDMS), polyethylene terephthalate (PET), polyvinylidene fluoride (PVDF), polyethersulfone (PES), polystyrene (PS), polycarbonate (PC), polyimide (PI), polyethylene naphthalate (PEN), polyarylate (PAR), or a combination thereof. Hereinafter, for the convenience of explanation, the first and second films P1 and P2 including PI will be described as a representative example.

The first and second films P1 and P2 are patterned to have a serpentine shape. When the first and second films P1 and P2 have the serpentine shape, the temperature sensor 20 is flexible, and thus the temperature sensor 20 can be prevented from being damaged even when the temperature sensor 20 is bent or curved due to external strain.

The first and second films P1 and P2 encapsulate the first and second electrodes E1 and E2 and the temperature sensing device 10 to support the structure of the temperature sensor 20 and to substantially simultaneously prevent the structure of the first and second electrodes E1 and E2 and the temperature sensing device 10 from being damaged. Accordingly, the reliability of the temperature sensor 20 is improved by the first and second films P1 and P2.

The first and second electrodes E1 and E2 are formed on the first film P1 to be spaced apart from each other.

The first and second electrodes E1 and E2 include a transparent or semi-transparent material. For instance, the first and second electrodes E1 and E2 can include indium tin oxide (ITO), indium zinc oxide (IZO), zinc oxide (ZnO), indium tin zinc oxide (ITZO), or a combination thereof. Hereinafter, for the convenience of explanation, the first and second electrodes E1 and E2 including ITO will be described as a representative example.

To improve the flexibility and the reliability of the temperature sensor 20, the first and second electrodes E1 and E2 are patterned to have a serpentine shape similar to that of the first and second films P1 and P2.

Detailed descriptions of the first and second films P1 and P2 and the first and second electrodes E1 and E2, each having the serpentine shape, will be described in detail with reference to FIG. 3.

The temperature sensing device 10 is formed on the first and second electrodes E1 and E2 and the first film P1 and the second film P2 are formed on the temperature sensing device 10. The temperature sensing device 10 will be described in detail with reference to FIG. 1.

As described above, since the elements included in the temperature sensor 20 are transparent or semi-transparent, the temperature sensor 20 can be transparent or semi-transparent and flexible due to the elements each having the serpentine structure.

Figure 3:
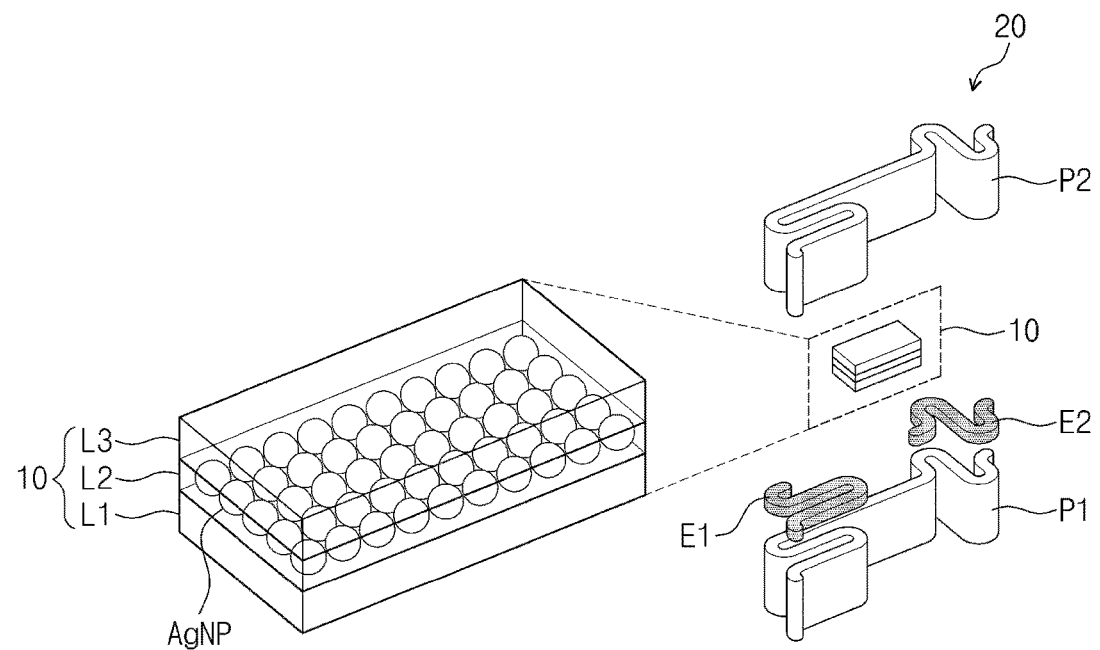
FIG. 3 is an exploded perspective view showing the temperature sensor shown in FIG. 2.

FIG. 3 is an exploded perspective view showing the temperature sensor 20 shown in FIG. 2.

Referring to FIG. 3, the first and second electrodes E1 and E2 having the serpentine structure are formed on the first film P1 having the serpentine structure, the temperature sensing device 10 is formed on the first film P1 and the first and second electrodes E1 and E2, and the second film P2 having the serpentine structure is formed on the temperature sensing device 10. Therefore, the temperature sensing device 10 and the first and second electrodes E1 and E2 are passivated by the first and second films P1 and P2.

The temperature sensor 20 includes at least one temperature sensing device 10. When the temperature sensor 20 includes the temperature sensing devices, the temperature sensing devices can be connected to each other by the first and second films P1 and P2 and the first and second electrodes E1 and E2, each having the serpentine structure.

Figure 4A:
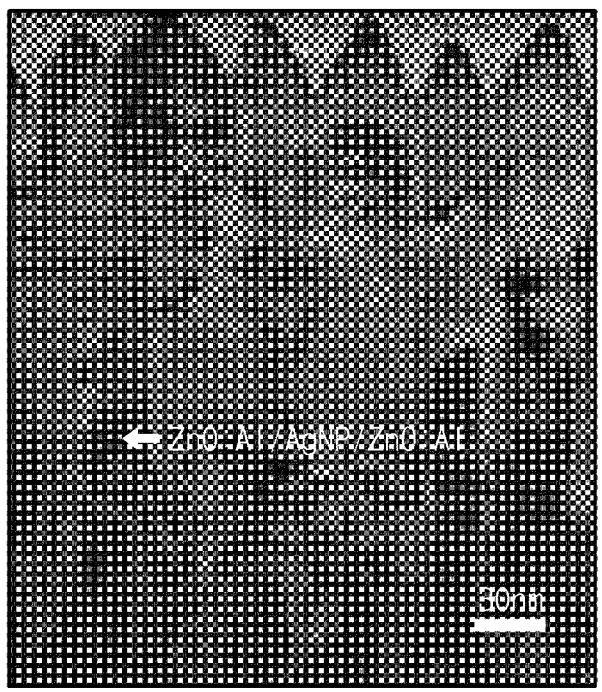
FIG. 4A is a transmission electron microscopy (TEM) image of a temperature sensing device.
Figure 4B:
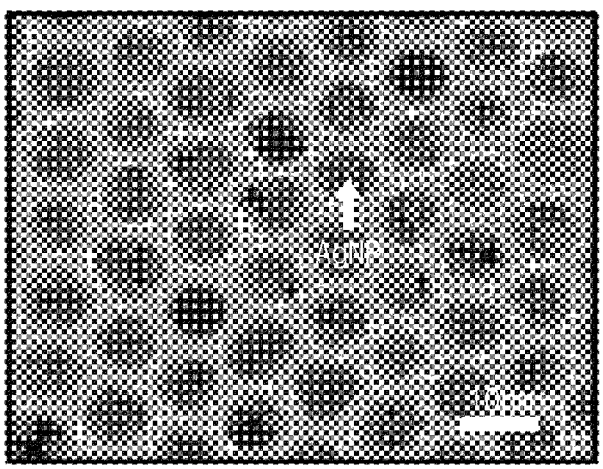
FIG. 4B is a TEM image of a second layer including silver nano-particles.

FIG. 4A is a transmission electron microscopy (TEM) image of a temperature sensing device and FIG. 4B is a TEM image of a second layer including silver nano-particles.

Referring to FIG. 4A, the cross-sectional structure of the temperature sensing device on which the first to third layers are sequentially stacked can be identified.

Referring to FIG. 4B, the silver nano-particles AgNP can be arranged in a line on the second layer and have substantially the same size. As described above, since the silver nano-particles AgNP are substantially uniformly arranged and have a substantially uniform size, the temperature sensor can have a structure with improved uniformity even when the temperature sensor is manufactured using the temperature sensing devices.

Figure 5A:
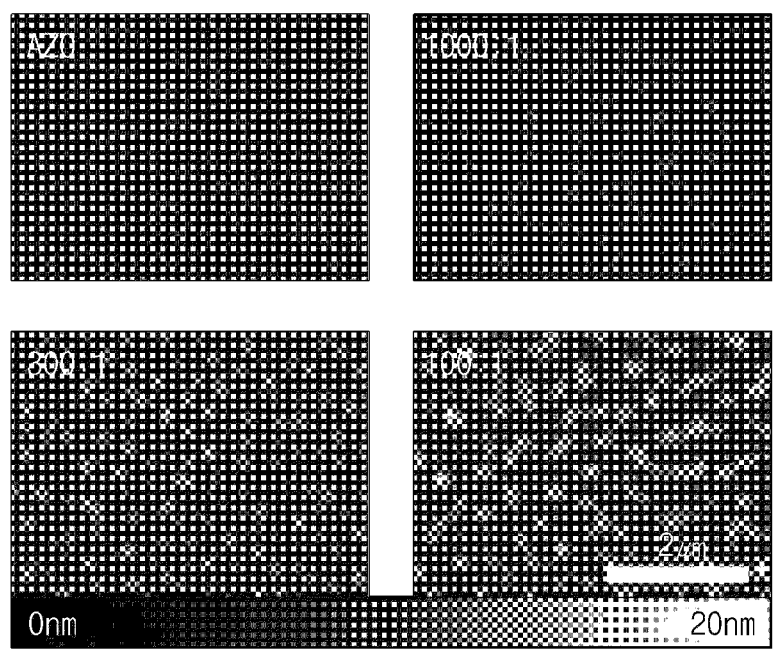
FIG. 5A illustrates atomic force microscopy (AFM) images of temperature sensing devices including the silver nano-particles at different dilution ratios.
Figure 5B:
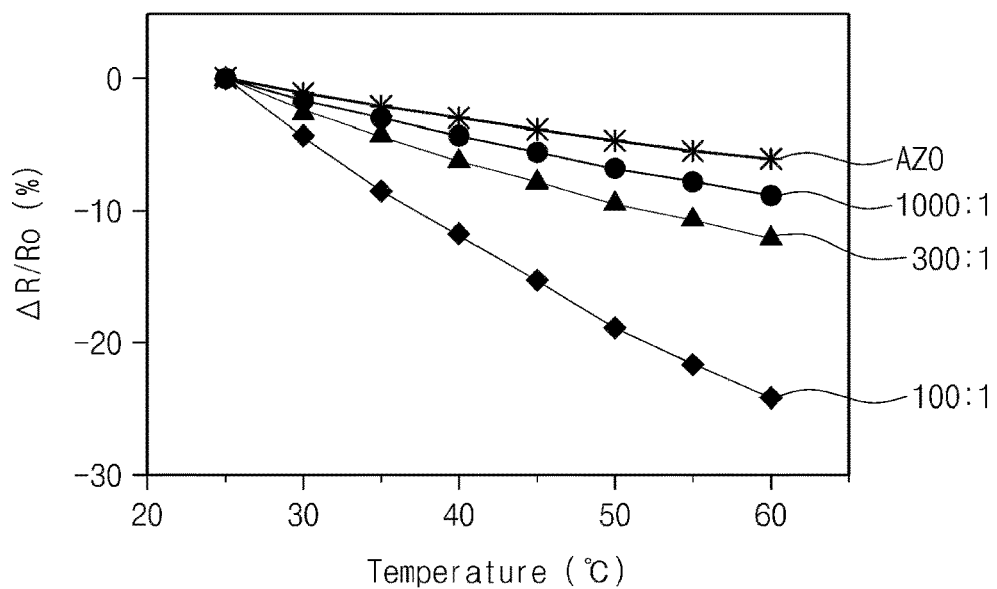
FIG. 5B is a graph showing a resistance variation of the temperature sensing device including the silver nano-particles at different dilution ratios as a function of a temperature.
Figure 5C:
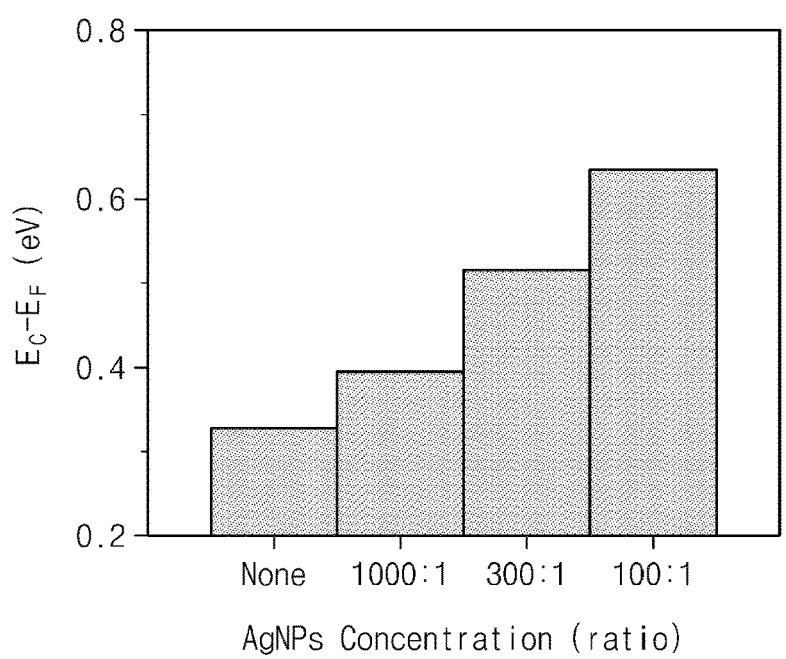
FIG. 5C is a result graph obtained by analyzing the temperature sensing device including the silver nano-particles at different dilution ratios using an ultraviolet photoelectron spectroscopy (UPS) and an ultraviolet spectroscopy (UVS).

FIG. 5A illustrates atomic force microscopy (AFM) images of temperature sensing devices including the silver nano-particles at different dilution ratios. FIG. 5B is a graph showing a resistance variation of the temperature sensing device including the silver nano-particles at different dilution ratios as a function of a temperature. FIG. 5C is a result graph obtained by analyzing the temperature sensing device including the silver nano-particles at different dilution ratios using an ultraviolet photoelectron spectroscopy (UPS) and an ultraviolet spectroscopy (UVS).

Referring to FIG. 5A, a first image AZO shows the AFM image of the temperature sensing device not including the silver nano-particles, a second image (1000:1) shows the AFM image of the temperature sensing device including the silver nano-particles diluted with a dilution ratio of about 1000:1, a third image (300:1) shows the AFM image of the temperature sensing device including the silver nano-particles diluted at a dilution ratio of about 300:1, and a fourth image (100:1) shows the AFM image of the temperature sensing device including the silver nano-particles diluted at a dilution ratio of about 100:1. As represented by the AFM images, the concentration of the silver nano-particles included in each temperature sensing device increases as the dilution ratio of the silver nano-particles included in each temperature sensing device decreases.

Referring to FIG. 5B, the slope of the graphs increases with the increase of the concentration of the silver nano-particles included in each temperature sensing device increases. For instance, the slope of the graph with respect to the temperature sensing device not including the silver nano-particles is about 0.096 (%/° C.) and the slope of the graph with respect to the temperature sensing device including the silver nano-particles diluted at the dilution ratio of about 100:1 is about 0.69 (%/° C.).

That is, as the concentration of the silver nano-particles included in each temperature sensing device increases, the sensitivity of the temperature sensing device with respect to temperature increases. Therefore, in order to manufacture a temperature sensing device that can precisely sense temperature, the concentration of the silver nano-particles included in the temperature sensing device can be increased.

The variation in resistance of the temperature sensing device in accordance with the temperature is related to a carrier density. As the carrier density of the temperature sensing device increases, the resistance decreases, and as the carrier density of the temperature sensing device decreases, the resistance increases. That is, the carrier density of the temperature sensing device is inversely proportional to the resistance of the temperature sensing device.

The carrier density of the temperature sensing device is obtained by the following Equation 1.

$$\ln n = \ln N_c - \frac{E_c - E_F}{kT} \quad \text{Equation 1}$$

In Equation 1, "n" denotes the carrier density, "Nc" denotes the effective density of the states function in the conduction band, "Ec" denotes the minimum energy level of the conduction band, "Ef" denotes the Fermi energy level, "k" denotes Boltzmann's constant, and "T" denotes the temperature.

According to Equation 1, Ec-Ef exerts an influence on the carrier density. In particular, as the value of Ec-Ef increases, the degree of the variation of the carrier density (n) in accordance with the variation of the temperature (T) increases.

Referring to FIG. 5C, when the dilution ratio of the silver nano-particles is reduced, the value (eV) of Ec-Ef increases.

According to Equation 1 and the analysis result shown in FIG. 5C, when the concentration of the silver nano-particles increases, the value (eV) of Ec-Ef increases, and as a result, the carrier density as a function of the temperature is varies greatly. That is, when the concentration of the silver nano-particles included in the temperature sensing device increases, the sensitivity of the temperature sensing device increases.

For the convenience of explanation, FIGS. 5A to 5C show the graphs obtained by analyzing the temperature sensing devices in which the silver nano-particles are diluted in the dilution ratios of about 1000:1, 300:1, and 100:1, respectively, but they should not be limited thereto or thereby. That is, the temperature sensing device can be manufactured to have various dilution ratios by taking use of the temperature sensor, manufacturing process, and manufacturing cost into consideration.

Hereinafter, for the convenience of explanation, the temperature sensing device including the silver nano-particles diluted at a dilution ratio of about 100:1 will be described in detail as a representative example.

Figure 6A:
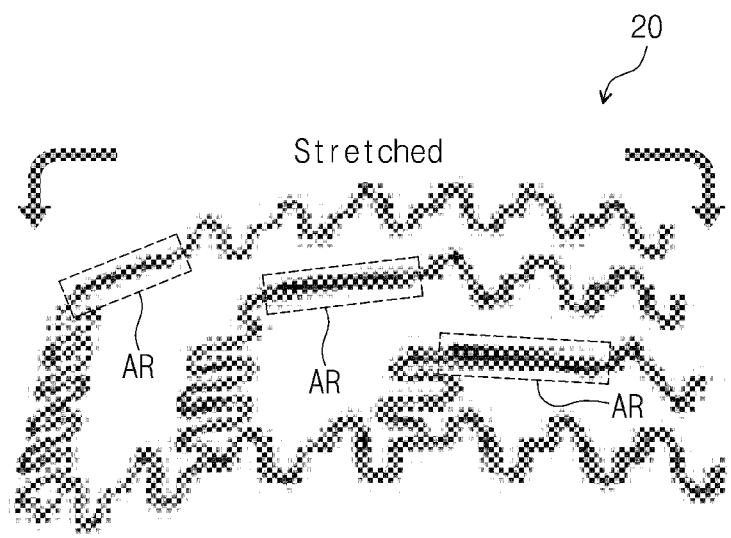
FIG. 6A is a finite-element analysis image of a temperature sensor stretched by external strain.
Figure 6B:
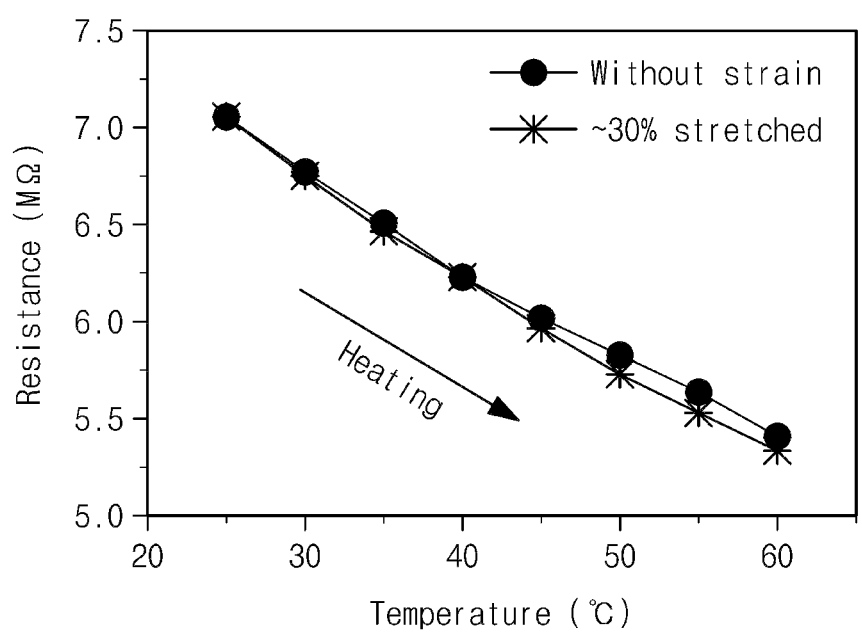
FIG. 6B is a graph showing a resistance characteristic of a temperature sensor stretched by external strain and a temperature sensor to which external strain is not applied as a function of a temperature variation.

FIG. 6A is a finite-element analysis image of a temperature sensor stretched by external strain and FIG. 6B is a graph showing a resistance characteristic of a temperature sensor stretched by external strain and a temperature sensor to which external strain is not applied as a function of a temperature variation.

Referring to FIG. 6A, the temperature sensor 20 includes an active region AR in which the temperature sensing device is included and an inactive region in which the temperature sensing device is not included. The inactive region includes the first and second electrodes and the first and second films, which have the serpentine structure. The serpentine structure of the inactive area enhances the flexibility of the temperature sensor 20, and substantially simultaneously relieves stress caused by the external strain. As a result, the stress caused by the external strain is not applied to the active region AR in which the temperature sensing device is arranged. Accordingly, although the external strain is applied to the temperature sensor 20, the temperature sensing device arranged in the active region AR is prevented from being easily damaged, and thus durability and reliability of the temperature sensor 20 are improved.

To test the durability and reliability of the temperature sensor 20, an experiment that measures the variation of the resistance in accordance with the variation of the temperature was carried out while the temperature sensor 20 was stretched by the external strain in a range from about 0.6% to about 30%.

Referring to FIG. 6B, there was no significant difference in the temperature sensing ability between the temperature sensor stretched by the external strain and the temperature sensor to which no external strain was applied. Therefore, the temperature sensor according to the present exemplary embodiment can be applied to a wearable device with variable shape and high flexibility without being restricted.

Figure 7A:
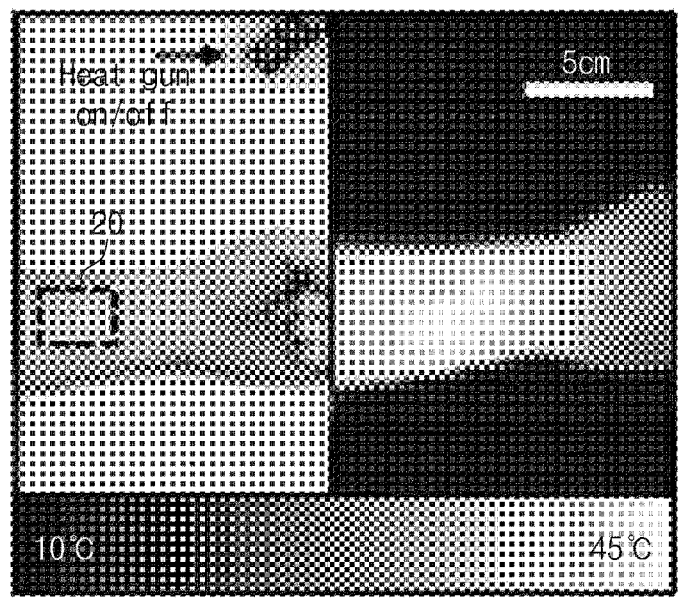
FIG. 7A is a view showing an experiment of applying heat to a temperature sensor using a heat gun.
Figure 7B:
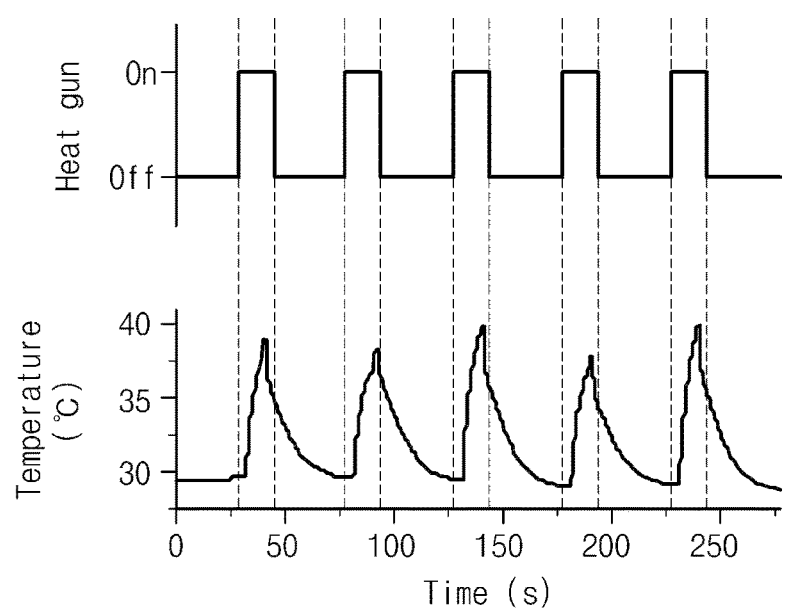
FIG. 7B is a result graph of the experiment shown in FIG. 7A.

FIG. 7A is a view showing an experiment of applying heat to a temperature sensor using a heat gun and FIG. 7B is a result graph of the experiment shown in FIG. 7A.

Referring to FIG. 7A, the temperature sensor 20 was repeatedly heated up and cooled down by periodically operating the heat gun (refer to the left image shown in FIG. 7A). When the heat gun was turned on to heat the temperature sensor 20, the temperature of the temperature sensor 20 and the wrist on which the temperature sensor 20 was worn was increased to about 40° C. The increase of the temperature of the temperature sensor 20 and the wrist could be monitored by an infrared ray camera (refer to the right image in FIG. 7A).

Referring to FIG. 7B, when the heat gun was turned on, the temperature sensed by the temperature sensor 20 was increased while the temperature sensor 20 was heated up, and when the heat gun was turned off, the temperature sensed by the temperature sensor 20 was decreased while the temperature sensor 20 was cooled down. In addition, the temperature sensor 20 could sense the same temperature as the temperature monitored by the infrared ray camera within a relatively fast response period from a time point at which the temperature sensor 20 was heated.

According to the above-mentioned experiment, the temperature sensor 20 can have a fast reaction speed and can precisely sense the temperature.

Figure 8A:
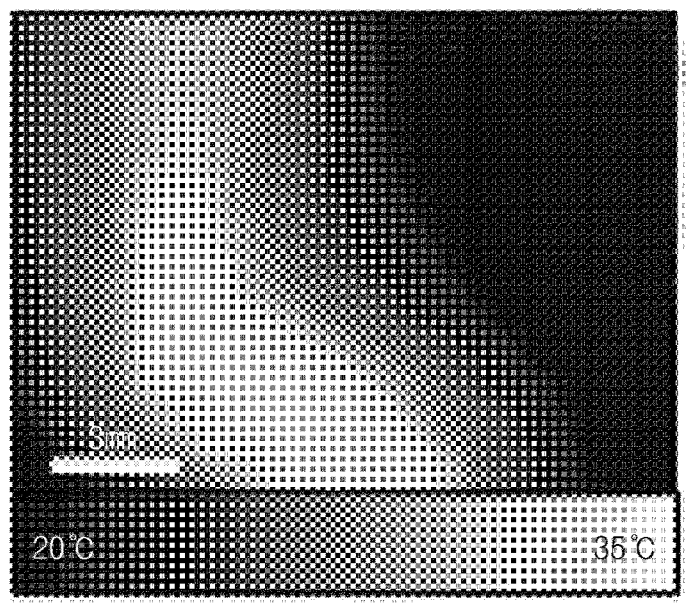
FIG. 8A is an image of a heater with different temperatures according to its areas, which was photographed by an infrared ray camera.
Figure 8B:
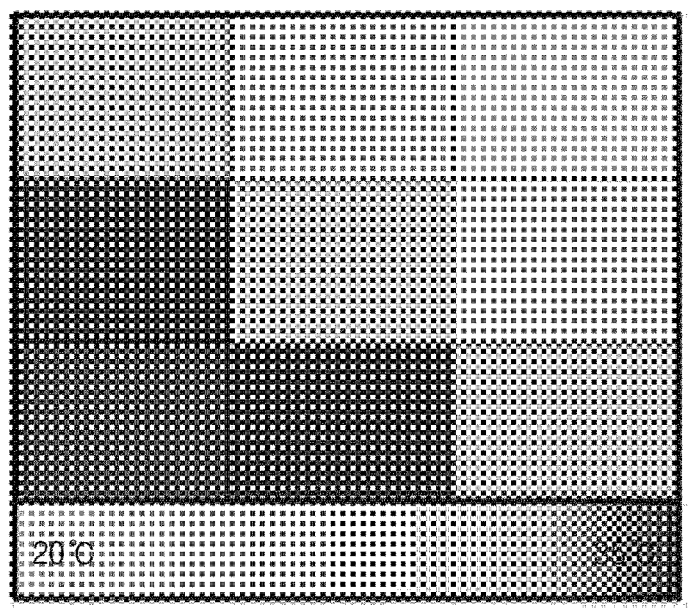
FIG. 8B is a view showing a sensing result of the temperature sensor of FIG. 8A.
Figure 8C:
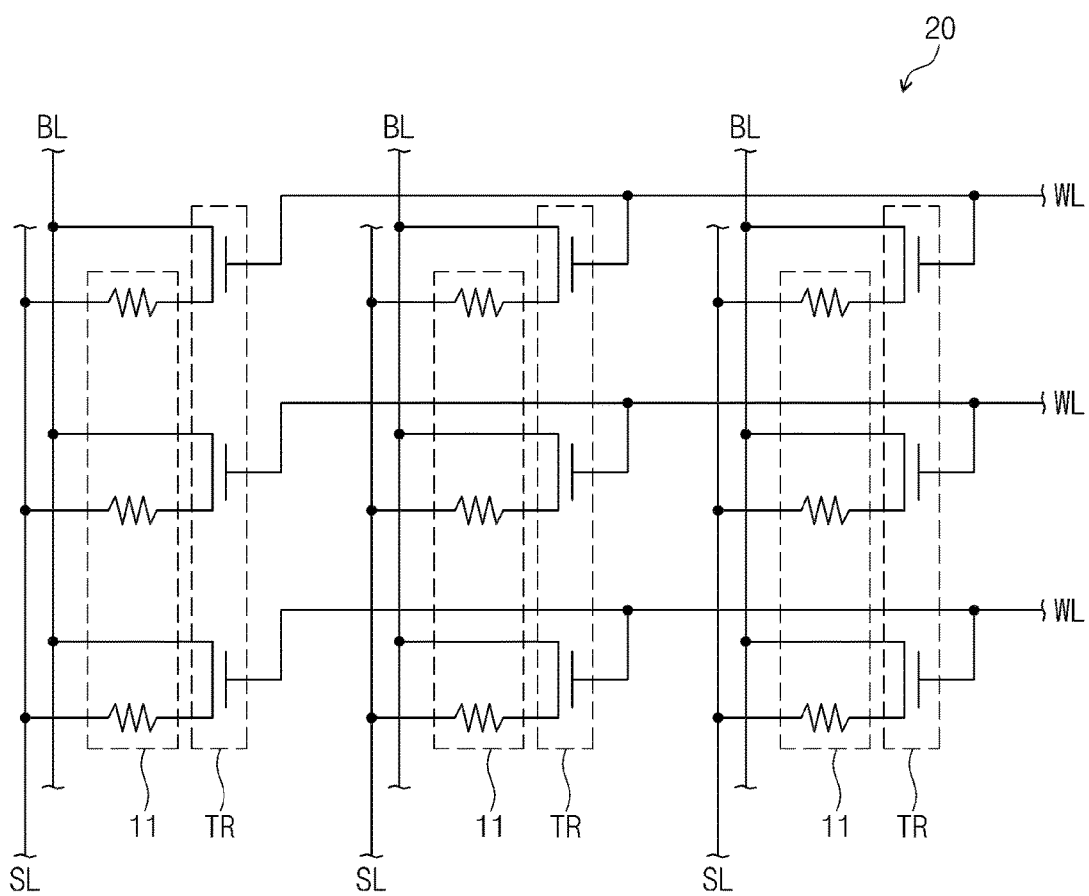
FIG. 8C is a circuit diagram showing a multi-channel temperature sensor.

FIG. 8A is an image of a heater with different temperatures by its areas, which was photographed by an infrared ray camera. FIG. 8B is a view showing a sensing result of the temperature sensor of FIG. 8A. FIG. 8C is a circuit diagram showing a multi-channel temperature sensor.

In the experiment related to FIGS. 8A and 8B, a temperature sensor with a 3×3 array multi-channel was configured to include a plurality of temperature sensing devices.

Referring to FIG. 8A, the areas of the heater having different temperatures were monitored by the infrared ray camera.

Referring to FIG. 8B, the temperature sensor arranged above the heater shown in FIG. 8A sensed the different temperatures by channels. In addition, the temperatures obtained by the infrared ray camera by the areas of the heater were substantially equal to the temperatures sensed by the temperature sensor by the channels.

Accordingly, a manufacturer can improve the temperature sensing ability of the temperature sensor according to the areas of the temperature sensor by increasing the number of channels of the temperature sensor in accordance with a manufacturing purpose, a manufacturing application, a manufacturing environment, etc.

Referring to FIG. 8C, the temperature sensor can have a multi-channel configuration and include a plurality of temperature sensing devices 11 and a plurality of switching devices TR, e.g., transistors, respectively connected to the temperature sensing devices 11. The circuit diagram shown in FIG. 8C shows the temperature sensor 20 with a 3×3 array multi-channel, but the temperature sensor 20 should not be limited to the 3×3 array multi-channel.

The temperature sensing devices 11 correspond to the temperature sensors 20 in a one-to-one correspondence. A first end of each of the temperature sensing devices 11 is connected to a source terminal of a corresponding switching device TR of the switching devices TR.

A drain terminal of each of the switching devices TR is electrically connected to a corresponding bit line BL and a second end of each of the temperature sensing devices 11 is electrically connected to a corresponding source line SL. A gate terminal of each of the switching devices TR is electrically connected to a corresponding word line WL. Each switching device TR is turned on in response to a switching on signal provided through the word line WL, and thus the bit line BL connected to the drain terminal of the switching device TR is electrically connected to the temperature sensing device 11 and the source line SL connected to the source terminal of the switching device TR. As a result, a signal generated by the temperature sensing device 11 is output from the temperature sensing device 11 through the bit line BL and/or the source line SL, which are/is connected to the temperature sensing device 11.

The switching devices TR connected to the same word line WL are substantially simultaneously turned on and the switching devices TR connected to different word lines are turned on at different time points. Therefore, the switching devices TR are grouped into groups in accordance with the word lines WL connected thereto and the switching device groups are sequentially operated.

To exactly and precisely sense the temperature, a multi-channel temperature sensor 20 including the temperature sensing devices 11 is required to be manufactured. When the temperature sensing devices 11 are arranged in a simple array form or matrix, signal interference occurs between the temperature sensing devices 11. To prevent the signal interference from occurring, the temperature sensing devices 11 are connected to the switching devices TR and sequentially operated, and thus, the signal interference between the temperature sensing devices 11 can be minimized.

Data about the temperature of each channel, which is sensed by the temperature sensor 20, can be determined by monitoring the output signal from each temperature sensing device 11. However, the temperature sensor 20 should not be limited to the circuit diagram shown in FIG. 8C.

As described above, the temperature sensor 20 is flexible and transparent or semi-transparent, and has a superior temperature sensing ability. Thus, the temperature sensor 20 according to the present exemplary embodiment can be applied to a wearable device that is spotlighted recently.

In the present exemplary embodiment, a wearable device generally refers to any electronic device that contacts or is worn on a portion of the user's body. For instance, the wearable device includes various devices, such as a head-mounted display, a skin-mounted wearable device, a smart watch, a smart ring, a wheelchair, etc. Hereinafter, as embodiments of the wearable device, the skin-mounted wearable device, the smart watch, and the wheelchair, each to which the piezoelectric sensor 30 is applied, will be described in detail.

Figure 9:
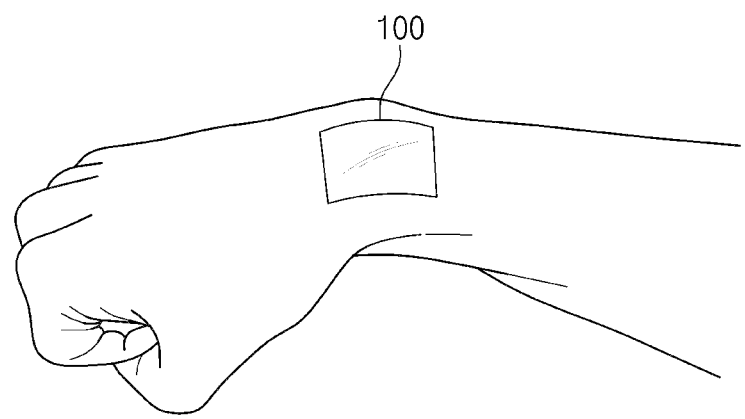
FIG. 9 is a view showing a skin-mounted wearable device manufactured using a temperature sensor.

FIG. 9 is a view showing a skin-mounted wearable device 100 manufactured using a temperature sensor.

Referring to FIG. 9, the skin-mounted wearable device 100 is manufactured by attaching the temperature sensor to a transparent or semi-transparent substrate, e.g., polydimethylsiloxane (PDMS), having an adhesive strength and which is flexible. The skin-mounted wearable device 100 can be used as a device to measure a user's body temperature in real-time.

In particular, the skin-mounted wearable device 100 is useful to measure the body temperature of acute stroke patients. Since an aura (symptom) of the acute stroke patients, e.g., a sudden body temperature drop, can be quickly monitored through the skin-mounted wearable device 100, the acute stroke patients can receive proper medical treatment as quickly as possible.

In addition, since the skin-mounted wearable device 100 is transparent or semi-transparent and it is difficult to be recognized by human eyes, the skin-mounted wearable device 100 is useful to hide the fact that the user is a patient.

To this end, the skin-mounted wearable device 100 can include additional elements, and the additional elements will be described in detail with reference to FIG. 10.

Figure 10:
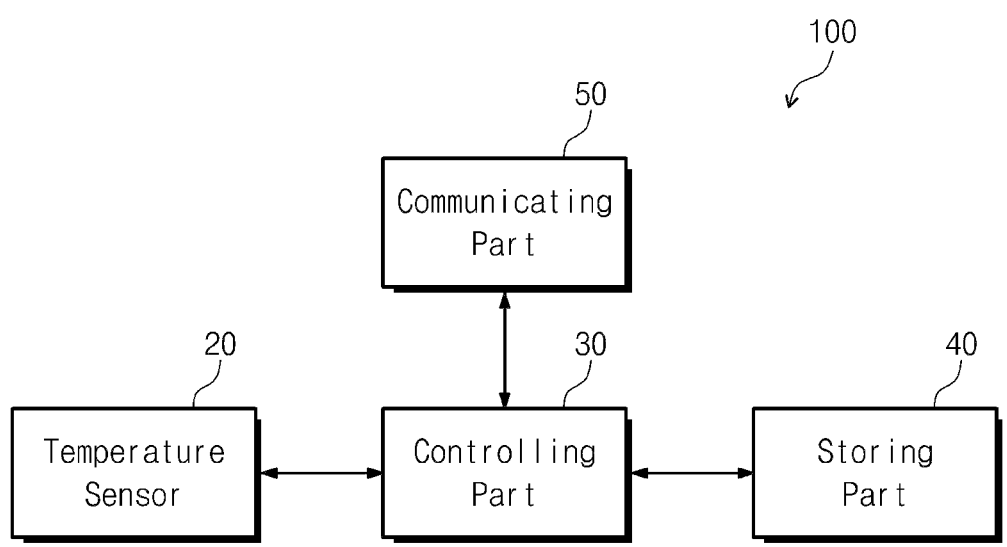
FIG. 10 is a block diagram showing the skin-mounted wearable device shown in FIG. 9.

FIG. 10 is a block diagram showing the skin-mounted wearable device 100 shown in FIG. 9.

Referring to FIG. 10, the skin-mounted wearable device 100 includes the temperature sensor 20, a storing part or memory 40, a communicating part of communication interface 50, and a controlling part or controller 30.

The temperature sensor 20 senses an ambient temperature, and details thereof are as described earlier.

The storing part 40 stores data. For instance, the storing part 40 can be, but is not limited to, a programmable read-only memory (ROM), an erasable programmable read-only memory (PROM), an erasable programmable read-only memory (EPROM), a dynamic random access memory (DRAM), a static random access memory (SRAM), or a non-volatile memory. In particular, the storing part 40 according to the present exemplary embodiment can communicate with other elements to receive and store various data. For instance, the storing part 40 receives data about the temperature sensed by the temperature sensor 20 from the controller 30 or the temperature sensor 20 and stores the data about the temperature in real-time.

The communicating part 50 can transmit and receive data to and from external devices through various protocols. The communicating part 50 can access a network through a wire or wireless communication system to transmit and receive various data to and from the external devices.

The controlling part 30 can communicate with the temperature sensor 20, the storing part 40, and the communicating part 50 to control the temperature sensor 20, the storing part 40, and the communicating part 50. Particularly, the controlling part 30 can sense the temperature using the temperature sensor 20 and performs various commands on the basis of the sensed temperature.

As an example, the controlling part 30 can monitor the body temperature of the user wearing the skin-mounted wearable device 100 using the temperature sensor 20. The controlling part 30 can check whether the body temperature sensed by the temperature sensor 20 is in a normal range. The normal range can vary depending on a patient's disease, a patient's condition, etc. For instance, when the user wearing the skin-mounted wearable device 100 is an acute stroke patient, the controlling part 30 can determine that whether the sensed body temperature is in the normal range on the basis of the rapid variation in the body temperature of the user during a predetermined time period.

When the sensed body temperature is in the normal range, the controlling part 30 can transmit the data about the body temperature of the user to the storing part 40 to allow the storing part 40 to store the body temperature of the user by time.

However, when the sensed body temperature is not in the normal range, the controlling part 30 can control the communicating part 30 to allow the communicating part 30 to communicate with the external device and transmits the data about a present body temperature of the user. Thus, the external device can be, but is not limited to, a communication unit installed in a hospital, a fire station, etc. As described above, the controlling part 30 can monitor the body temperature of the user in real-time and instantly communicate with the external device when the controller part 30 senses warning signals from the user, and thus the user can receive proper medical treatment as quickly as possible.

Meanwhile, the elements 20, 30, 40, and 50 of the skin-mounted wearable device 10 shown in FIG. 10 are separated from each other, but the elements 20, 30, 40, and 50 of the skin-mounted wearable device 10 can be integrated in a single or multiple chips in accordance with a design rule.

Figure 11:
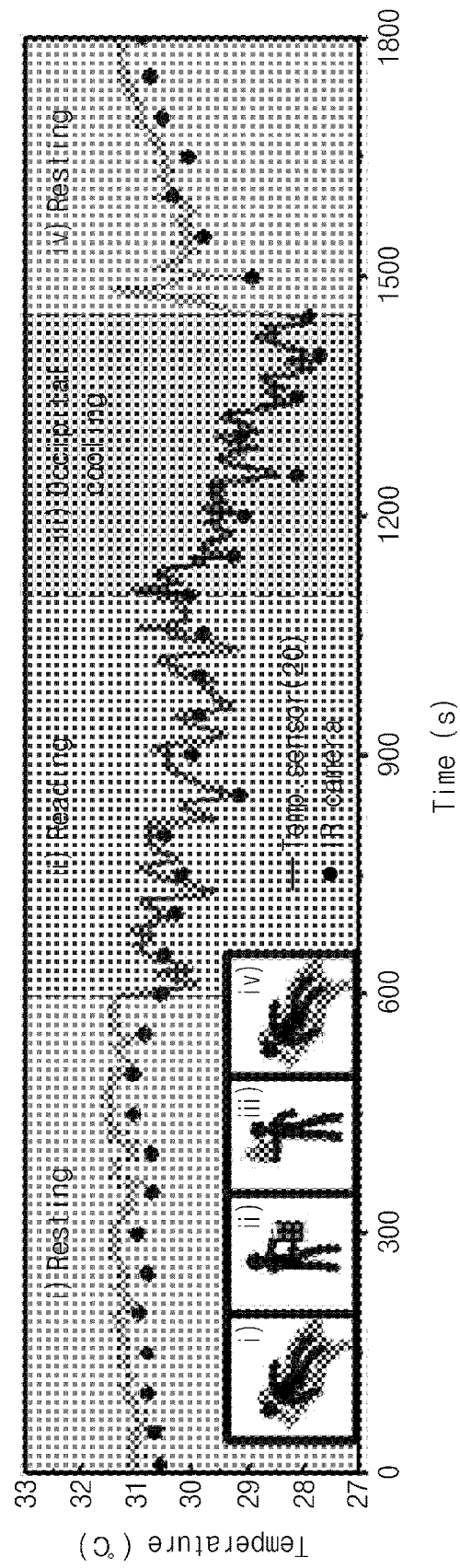
FIG. 11 is a graph showing a variation in body temperature of an acute stroke patient who is wearing the skin-mounted wearable device for a day.

FIG. 11 is a graph showing a variation in body temperature of the acute stroke patient who is wearing the skin-mounted wearable device for a day.

To precisely monitor the body temperature of the patient, the skin-mounted wearable device was attached to a skin corresponding to a radial artery of the patient. In addition, the body temperature of the user was measured by the infrared ray camera in real-time to verify whether the skin-mounted wearable device precisely monitors the body temperature of the user or not.

Referring to FIG. 11, the variation in body temperature of the user, which was recorded by the skin-mounted wearable device, nearly corresponded to the variation in body temperature of the user, which was measured by the infrared ray camera. In addition, a small variation in body temperature of the user was precisely monitored and the reaction speed compared to the temperature variation was very fast.

In the present exemplary embodiment, the skin-mounted wearable device is described as a representative example, but the temperature sensor can be applied to various wearable devices as long as the wearable devices are attached to a portion of the user's body or to various temperature measuring devices required to quickly and precisely sense the temperature variation.

Although the exemplary embodiments of the inventive technology have been described, it is understood that the present invention should not be limited to these exemplary embodiments but various changes and modifications can be made by one ordinary skilled in the art within the spirit and scope of the inventive technology as hereinafter claimed.

What is claimed is:

1. A wearable device, comprising:
   a temperature sensor configured to sense temperature; and
   a controller configured to: i) detect the temperature using the temperature sensor and ii) carry out a command corresponding to the sensed temperature,
   wherein the temperature sensor comprises:
   a first film that is flexible;
   a first electrode formed over the first film;
   a second electrode formed over the first film and spaced apart from the first electrode;
   a first layer formed over the first film, the first electrode, and the second electrode, wherein the first layer comprises a temperature sensing material and wherein the resistance of the temperature sensing material is configured to vary in response to changes in temperature;
   a second layer formed over the first layer and comprising silver nano-particles; and
   a third layer formed over the second layer and comprising the temperature sensing material; and
   a second film formed over the third layer.

2. The wearable device of claim 1, wherein the first and second electrodes have a serpentine structure.

3. The wearable device of claim 1, wherein the first and second films have a serpentine structure.

4. The wearable device of claim 1, wherein the temperature sensing device is transparent or semi-transparent.

5. The wearable device claim 1, wherein the temperature sensing material comprises zinc oxide ($ZnO_x$) doped with aluminum oxide ($Al_2O_3$).

6. The wearable device of claim 5, wherein the zinc oxide ($ZnO_x$) of the temperature sensing material is doped with the aluminum oxide at about 1 wt %.

7. The wearable device of claim 1, wherein the silver nano-particles of the second layer are diluted with a substantially constant dilution ratio.

8. The wearable device of claim 7, wherein the silver nano-particles of the second layer are diluted with a dilution ratio of about 1000:1 to about 10:1.

9. The wearable device of claim 1, further comprising a memory configured to store temperature data, wherein the controller is further configured to control the memory to store the detected temperature as a function of time when the detected temperature using the temperature sensor is in a normal range.

10. The wearable device of claim 9, further comprising a communication interface configured to communicate with an external device, wherein the controller is further configured to communicate with the external device through the communication interface when the detected temperature using the temperature sensor is not in the normal range.

* * * * *